US012017077B2

(12) United States Patent
Kothandaraman et al.

(10) Patent No.: US 12,017,077 B2
(45) Date of Patent: Jun. 25, 2024

(54) SYSTEM AND METHOD FOR IDENTIFYING AVAILABILITY OF CLINICIAN DEFINED PROGRAMMING SETTINGS FOR A PATIENT

(71) Applicant: Boston Scientific Neuromodulation Corporation, Valencia, CA (US)

(72) Inventors: Sridhar Kothandaraman, Valencia, CA (US); Mun Pook Lui, Northridge, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 881 days.

(21) Appl. No.: 17/023,156

(22) Filed: Sep. 16, 2020

(65) Prior Publication Data

US 2020/0406043 A1 Dec. 31, 2020

Related U.S. Application Data

(63) Continuation of application No. 13/971,745, filed on Aug. 20, 2013, now Pat. No. 10,828,495.

(Continued)

(51) Int. Cl.
*A61N 1/372* (2006.01)
*A61N 1/36* (2006.01)
(Continued)

(52) U.S. Cl.
CPC ....... *A61N 1/37247* (2013.01); *A61N 1/3605* (2013.01); *A61N 1/37264* (2013.01);
(Continued)

(58) Field of Classification Search
CPC ............ A61N 1/37247; A61N 1/37264; A61N 1/36132; A61N 1/36146
See application file for complete search history.

(56) References Cited

U.S. PATENT DOCUMENTS 6,516,227 B1 2/2003 Meadows et al.
6,895,280 B2 5/2005 Meadows et al.
(Continued)

FOREIGN PATENT DOCUMENTS

AU 2013309216 B2 6/2017
EP 2890452 A1 7/2015
(Continued)

OTHER PUBLICATIONS

"U.S. Appl. No. 13/971,745, Pre-Appeal Brief Request filed Jan. 3, 2018", 5 pgs.

(Continued)

*Primary Examiner* — Tammie K Marlen
(74) *Attorney, Agent, or Firm* — Schwegman Lundberg & Woessner, P.A.

(57) ABSTRACT

An external control device for indicating whether a stimulation parameter set for use in a neurostimulator is available on a remote control in communication with the external control device is provided. The device includes a user interface configured for displaying the stimulation parameter set and an indicator that indicates whether the stimulation parameter set is available to the patient from the remote control. The device also includes control circuitry configured for, in response to input from the user (e.g., actuating the indicator), selectively turning the indicator on or off. The indicator may be an icon, and the icon may be a graphical depiction of a remote control. The user interface may be further configured for receiving additional input from the user, and the control circuitry may be further configured for, in response to the additional input from the user, programming the remote control with the stimulation parameter set.

20 Claims, 9 Drawing Sheets

Related U.S. Application Data (60) Provisional application No. 61/694,702, filed on Aug. 29, 2012.

(51) Int. Cl.
  *A61B 5/00* (2006.01)
  *A61B 18/00* (2006.01)

(52) U.S. Cl.
  CPC ....... *A61B 5/00* (2013.01); *A61B 2018/00577* (2013.01); *A61N 1/36132* (2013.01); *A61N 1/36146* (2013.01)

(56) References Cited

U.S. PATENT DOCUMENTS

| | | | |
|---|---|---|---|
| 6,993,384 | B2 | 1/2006 | Bradley et al. |
| 2003/0177031 | A1 | 9/2003 | Malek |
| 2005/0143781 | A1 | 6/2005 | Carbunaru et al. |
| 2007/0129774 | A1 | 6/2007 | Bourget et al. |
| 2008/0221644 | A1 | 9/2008 | Vallapureddy et al. |
| 2009/0082640 | A1 | 3/2009 | Kovach et al. |
| 2010/0010566 | A1 | 1/2010 | Thacker et al. |
| 2010/0121409 | A1 | 5/2010 | Kothandaraman et al. |
| 2011/0004275 | A1 | 1/2011 | Carbunaru et al. |
| 2011/0172737 | A1 | 7/2011 | Davis et al. |
| 2011/0282414 | A1 | 11/2011 | Kothandaraman et al. |
| 2012/0277823 | A1 | 11/2012 | Gerber et al. |
| 2012/0290041 | A1* | 11/2012 | Kim .................. A61N 1/36071 607/46 |
| 2013/0158628 | A1 | 6/2013 | Kothandaraman |
| 2013/0197607 | A1 | 8/2013 | Wilder et al. |
| 2014/0067015 | A1 | 3/2014 | Kothandaraman et al. |

FOREIGN PATENT DOCUMENTS

| | | |
|---|---|---|
| EP | 2890452 B1 | 2/2017 |
| WO | WO-2014035731 | 3/2014 |

OTHER PUBLICATIONS

"U.S. Appl. No. 13/971,745, Advisory Action dated Aug. 7, 2019", 3 pgs.
"U.S. Appl. No. 13/971,745, Advisory Action dated Nov. 18, 2016", 3 pgs.
"U.S. Appl. No. 13/971,745, Examiner Interview Summary dated May 17, 2019", 3 pgs.
"U.S. Appl. No. 13/971,745, Final Office Action dated Mar. 8, 2019", 9 pgs.
"U.S. Appl. No. 13/971,745, Final Office Action dated Jul. 14, 2016", 13 pgs.
"U.S. Appl. No. 13/971,745, Final Office Action dated Nov. 3, 2017", 14 pgs.
"U.S. Appl. No. 13/971,745, Non Final Office Action dated Jan. 7, 2020", 9 pgs.
"U.S. Appl. No. 13/971,745, Non Final Office Action dated Aug. 27, 2018", 9 pgs.
"U.S. Appl. No. 13/971,745, Non Final Office Action dated Nov. 23, 2015", 9 pgs.
"U.S. Appl. No. 13/971,745, Notice of Allowance dated Jul. 8, 2020", 10 pgs.
"U.S. Appl. No. 13/971,745, Response filed Feb. 18, 2016 to Non Final Office Action dated Nov. 23, 2016", 10 pgs.
"U.S. Appl. No. 13/971,745, Response filed Apr. 1, 2020 to Non Final Office Action dated Jan. 7, 2020", 12 pgs.
"U.S. Appl. No. 13/971,745, Response filed Jun. 10, 2019 to Final Office Action dated Mar. 8, 2019", 9 pgs.
"U.S. Appl. No. 13/971,745, Response filed Jun. 21, 2017 to Non Final Office Action dated Mar. 22, 2017", 9 pgs.
"U.S. Appl. No. 13/971,745, Response filed Oct. 14, 2016 to Final Office Action dated Jul. 14, 2016", 7 pgs.
"U.S. Appl. No. 13/971,745, Response filed Nov. 26, 2018 to Non Final Office Action dated Aug. 27, 2018", 9 pgs.
"U.S. Appl. No. 3/971,745, Non Final Office Action dated Mar. 22, 2017", 14 pgs.
"Australian Application Serial No. 2013309216, First Examiner Report dated Apr. 20, 2016", 5 pgs.
"Australian Application Serial No. 2013309216, Response filed Jan. 10, 2017 to First Examiner Report dated Apr. 20, 2016", 6 pgs.
"International Application Serial No. PCT/US2013/055878, International Preliminary Report on Patentability dated Mar. 12, 2015", 7 pgs.
"International Application Serial No. PCT/US2013/055878, International Search Report dated Nov. 4, 2013", 4 pgs.
"International Application Serial No. PCT/US2013/055878, Written Opinion dated Nov. 4, 2013", 5 pgs.

* cited by examiner

SYSTEM AND METHOD FOR IDENTIFYING AVAILABILITY OF CLINICIAN DEFINED PROGRAMMING SETTINGS FOR A PATIENT

RELATED APPLICATION DATA

The present application is a continuation of U.S. application Ser. No. 16/168,578, filed Oct. 23, 2018, which claims the benefit under 35 U.S.C. § 119 to U.S. provisional patent application Ser. No. 61/694,702, filed Aug. 29, 2012. The foregoing applications are hereby incorporated by reference into the present application in their entireties.

FIELD OF THE INVENTION

The present invention relates to tissue stimulation systems, and more particularly, to a system and method for programming an implantable tissue stimulator.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis and incontinence. Deep Brain Stimulation (DBS) has also been applied therapeutically for well over a decade for the treatment of refractory chronic pain syndromes, and DBS has also recently been applied in additional areas such as movement disorders and epilepsy. Further, in recent investigations, Peripheral Nerve Stimulation (PNS) systems have demonstrated efficacy in the treatment of chronic pain syndromes and incontinence, and a number of additional applications are currently under investigation. Also, Functional Electrical Stimulation (FES) systems such as the Freehand system by NeuroControl (Cleveland, Ohio) have been applied to restore some functionality to paralyzed extremities in spinal cord injury patients.

These implantable neurostimulation systems typically include one or more electrode carrying neurostimulation leads, which are implanted at the desired stimulation site, and a neurostimulator (e.g., an implantable pulse generator (IPG)) implanted remotely from the stimulation site, but coupled either directly to the neurostimulation lead(s) or indirectly to the neurostimulation lead(s) via a lead extension. Thus, electrical pulses can be delivered from the neurostimulator to the neurostimulation leads to stimulate the tissue and provide the desired efficacious therapy to the patient.

The combination of electrodes used to deliver electrical pulses to the targeted tissue constitutes an electrode combination, with the electrodes capable of being selectively programmed to act as anodes (positive), cathodes (negative), or left off (zero). In other words, an electrode combination represents the polarity being positive, negative, or zero. Other parameters that may be controlled or varied include the amplitude, width, and rate of the electrical pulses provided through the electrode array. Each electrode combination, along with the electrical pulse parameters, can be referred to as a "stimulation parameter set."

The neurostimulation system may further include a handheld patient programmer in the form of a remote control (RC) to remotely instruct the neurostimulator to generate electrical stimulation pulses in accordance with selected stimulation parameters. The RC may, itself, be programmed by a clinician, for example, by using a clinician's programmer (CP), which typically includes a general purpose computer, such as a laptop, with a programming software package installed thereon.

During programming, the clinician may use the CP to test several different stimulation parameter sets. In a typical scenario, the clinician utilizes a "stimulation parameter testing" screen of the CP to test the various stimulation parameter sets, and then, once the optimum or most effective stimulation parameter sets are determined, they are programmed into the IPG. Various stimulation parameter sets, also referred to as "areas," may be combined into a stimulation program that can be stored in the IPG. For example, four stimulation parameter sets may be combined into a single stimulation program, which, when operated via prompting by the RC, outputs four electrical pulse trains in accordance with the respective stimulation parameter sets via multiple timing channels. Although the IPG may be programmed with a stimulation program containing a number of stimulation parameter sets, not all of these stimulation parameter sets may be available to the patient. In particular, the RC may be programmed in a manner that prevents the patient from operating certain selected stimulation parameter sets that have been stored in the IPG. However, there is no easy way for the clinician to determine which of the stimulation parameter sets is available to the patient from the RC.

There, thus, remains a need to provide a user interface capable of easily and conveniently identifying those stimulation parameter sets that have already been made available through the RC, and capable of easily and conveniently indicating which stimulation parameter sets should be made available or unavailable through the RC.

SUMMARY OF THE INVENTION

In accordance with one aspect of the present inventions, an external control device for indicating whether a stimulation parameter set for use in a neurostimulator is available on a remote control in communication with the external control device is provided. The external control device includes a user interface configured for receiving input from a user, for displaying the stimulation parameter set, and for displaying an indicator that indicates whether the stimulation parameter set is available to the patient from the remote control. The indicator may be an icon, and the icon may be a graphical depiction of a remote control. The user interface may include a mouse, a trackball, a touchpad, and/or a joystick for receiving the input from the user. The user interface may include a digitizer screen for receiving the input from the user.

The external control device also includes control circuitry configured for, in response to input from the user (e.g., actuating the indicator), selectively turning the indicator on or off. The user interface may be further configured for receiving additional input from the user, and the control circuitry may be further configured for, in response to the additional input from the user, programming the remote control with the stimulation parameter set. The control circuitry may be further configured for, in response to the additional input from the user, programming the neurostimulator and/or remote control with the stimulation parameter set. The user interface may be configured for displaying a plurality of stimulation parameter sets and a respective plurality of indicators, each indicating whether the respective stimulation parameter set is available to the patient from the remote control, wherein the control circuitry may be further configured for, in response to input from the user, selectively turning each of the indicators on or off. The control circuitry may be configured for programming the plurality of stimulation parameter sets within a single program into the remote control.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings.

Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

The description that follows relates to a spinal cord stimulation (SCS) system. However, it is to be understood that the while the invention lends itself well to applications in SCS, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neural stimulator configured to treat urinary incontinence, sleep apnea, shoulder sublaxation, headache, etc.

Figure 1:
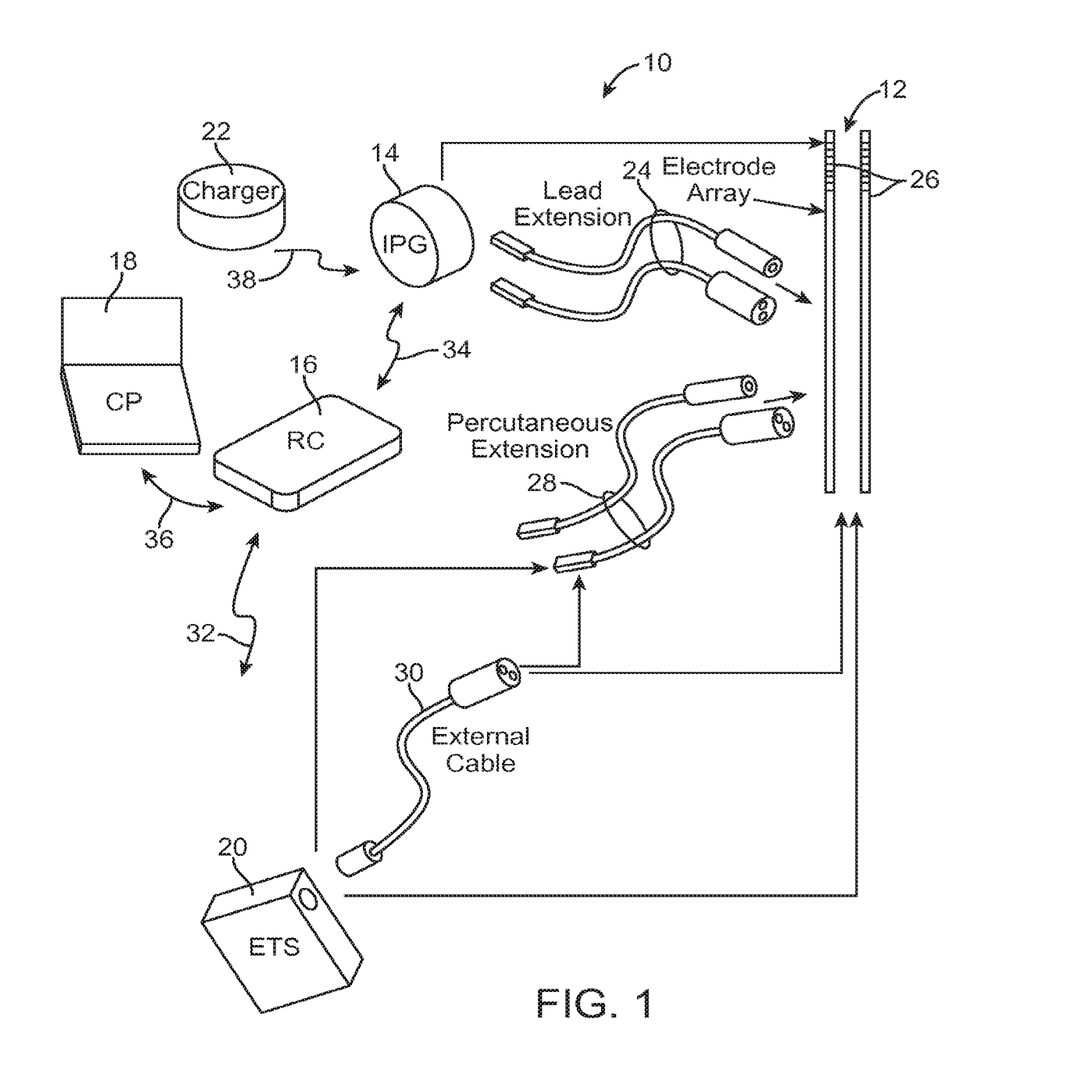
FIG. 1 is perspective view of one embodiment of a SCS system arranged in accordance with the present inventions.

Turning first to FIG. 1, an exemplary SCS system 10 generally includes a plurality (in this case, two) of implantable neurostimulation leads 12, an implantable pulse generator (IPG) 14, an external remote controller (RC) 16, a clinician's programmer (CP) 18, an external trial stimulator (ETS) 20, and an external charger 22.

The IPG 14 is physically connected via one or more percutaneous lead extensions 24 to the neurostimulation leads 12, which carry a plurality of electrodes 26 arranged in an array. In the illustrated embodiment, the neurostimulation leads 12 are percutaneous leads, and to this end, the electrodes 26 are arranged in-line along the neurostimulation leads 12. The number of neurostimulation leads 12 illustrated is two, although any suitable number of neurostimulation leads 12 can be provided, including only one. Alternatively, a surgical paddle lead in can be used in place of one or more of the percutaneous leads. As will be described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters.

The ETS 20 may also be physically connected via percutaneous lead extensions 28 and/or an external cable 30 to the neurostimulation leads 12. The ETS 20, which has pulse generation circuitry similar to that of the IPG 14, also delivers electrical stimulation energy in the form of a pulsed electrical waveform to the electrode array 26 accordance with a set of stimulation parameters. The major difference between the ETS 20 and the IPG 14 is that the ETS 20 is a non-implantable device that is used on a trial basis after the neurostimulation leads 12 have been implanted and prior to implantation of the IPG 14, to test the responsiveness of the stimulation that is to be provided. Thus, any functions described herein with respect to the IPG 14 can likewise be performed with respect to the ETS 20. Further details of an exemplary ETS are described in U.S. Pat. No. 6,895,280, which is expressly incorporated herein by reference.

The RC 16 may be used to telemetrically control the ETS 20 via a bi-directional RF communications link 32. Once the IPG 14 and neurostimulation leads 12 are implanted, the RC 16 may be used to telemetrically control the IPG 14 via a bi-directional RF communications link 34. Such control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. As will be described in further detail below, the CP 18 provides clinician detailed stimulation parameters for programming the IPG 14 and ETS 20 in the operating room and in follow-up sessions.

The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown). The clinician detailed stimulation parameters provided by the CP 18 are also used to program the RC 16, so that the stimulation parameters can be subsequently modified by operation of the RC 16 in a stand-alone mode (i.e., without the assistance of the CP 18).

The external charger 22 is a portable device used to transcutaneously charge the IPG 14 via an inductive link 38. For purposes of brevity, the details of the external charger 22 will not be described herein. Details of exemplary embodiments of external chargers are disclosed in U.S. Pat. No. 6,895,280, which has been previously incorporated herein by reference. Once the IPG 14 has been programmed, and its power source has been charged by the external charger 22 or otherwise replenished, the IPG 14 may function as programmed without the RC 16 or CP 18 being present.

Figure 2:
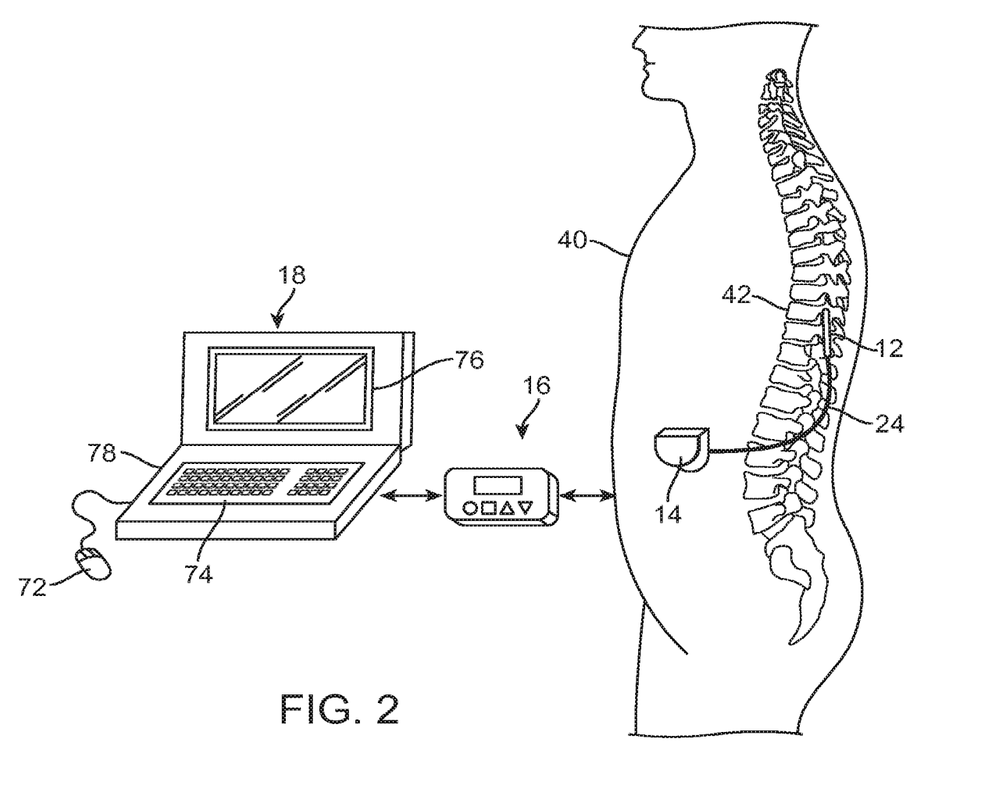
FIG. 2 is a plan view of the SCS system of FIG. 1 in use with a patient.

As shown in FIG. 2, the neurostimulation leads 12 are implanted within the spinal column 42 of a patient 40. The preferred placement of the neurostimulation leads 12 is adjacent, i.e., resting upon, the spinal cord area to be stimulated. Due to the lack of space near the location where the neurostimulation leads 12 exit the spinal column 42, the IPG 14 is generally implanted in a surgically-made pocket either in the abdomen or above the buttocks. The IPG 14 may, of course, also be implanted in other locations of the patient's body. The lead extension 24 facilitates locating the IPG 14 away from the exit point of the neurostimulation leads 12. As there shown, the CP 18 communicates with the IPG 14 via the RC 16.

Figure 3:
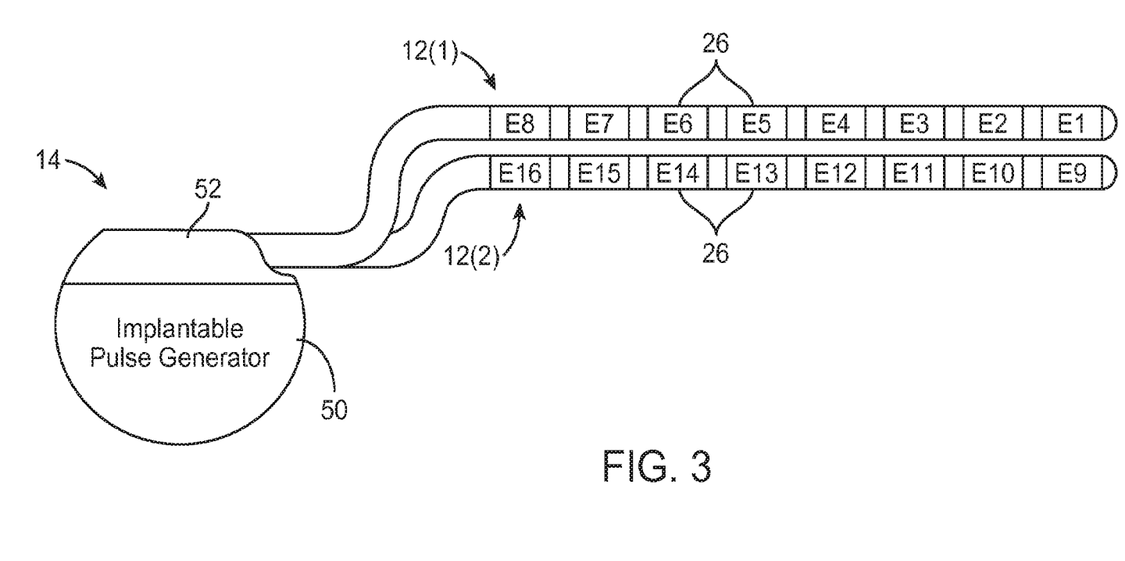
FIG. 3 is a side view of an implantable pulse generator and a pair of stimulation leads that can be used in the SCS system of FIG. 1.

Referring now to FIG. 3, the external features of the neurostimulation leads 12 and the IPG 14 will be briefly described. One of the neurostimulation leads 12(1) has eight electrodes 26 (labeled E1-E8), and the other stimulation lead 12(2) has eight electrodes 26 (labeled E9-E16). The actual number and shape of leads and electrodes will, of course, vary according to the intended application. The IPG 14 comprises an outer case 50 for housing the electronic and other components (described in further detail below), and a connector 52 to which the proximal ends of the neurostimulation leads 12 mate in a manner that electrically couples the electrodes 26 to the electronics within the outer case 50. The outer case 50 is composed of an electrically conductive, biocompatible material, such as titanium, and forms a hermetically sealed compartment wherein the internal electronics are protected from the body tissue and fluids. In some cases, the outer case 50 may serve as an electrode.

The IPG 14 includes a battery and pulse generation circuitry that delivers the electrical stimulation energy in the form of a pulsed electrical waveform to the electrode array 26 in accordance with a set of stimulation parameters programmed into the IPG 14. Such stimulation parameters may comprise electrode combinations, which define the electrodes that are activated as anodes (positive), cathodes (negative), and turned off (zero), percentage of stimulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse width (measured in microseconds), and pulse rate (measured in pulses per second).

Electrical stimulation will occur between two (or more) activated electrodes, one of which may be the IPG case 50. Simulation energy may be transmitted to the tissue in a monopolar or multipolar (e.g., bipolar, tripolar, etc.) fashion. Monopolar stimulation occurs when a selected one of the lead electrodes 26 is activated along with the case 50 of the IPG 14, so that stimulation energy is transmitted between the selected electrode 26 and case 50. Bipolar stimulation occurs when two of the lead electrodes 26 are activated as anode and cathode, so that stimulation energy is transmitted between the selected electrodes 26. For example, electrode E3 on the first lead 12(1) may be activated as an anode at the same time that electrode E11 on the second lead 12(2) is activated as a cathode. Tripolar stimulation occurs when three of the lead electrodes 26 are activated, two as anodes and the remaining one as a cathode, or two as cathodes and the remaining one as an anode. For example, electrodes E4 and E5 on the first lead 12(1) may be activated as anodes at the same time that electrode E12 on the second lead 12(2) is activated as a cathode.

In the illustrated embodiment, the IPG 14 can individually control the magnitude of electrical current flowing through each of the electrodes. In this case, it is preferred to have a current generator, wherein individual current-regulated amplitudes from independent current sources for each electrode may be selectively generated. Although this system is optimal to take advantage of the invention, other stimulators that may be used with the invention include stimulators having voltage regulated outputs. While individually programmable electrode amplitudes are optimal to achieve fine control, a single output source switched across electrodes may also be used, although with less fine control in programming. Mixed current and voltage regulated devices may also be used with the invention. Further details discussing the detailed structure and function of IPGs are described more fully in U.S. Pat. Nos. 6,516,227 and 6,993,384, which are expressly incorporated herein by reference.

It should be noted that rather than an IPG, the SCS system 10 may alternatively utilize an implantable receiver-stimulator (not shown) connected to the neurostimulation leads 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the stimulation in accordance with the control signals.

Figure 4:
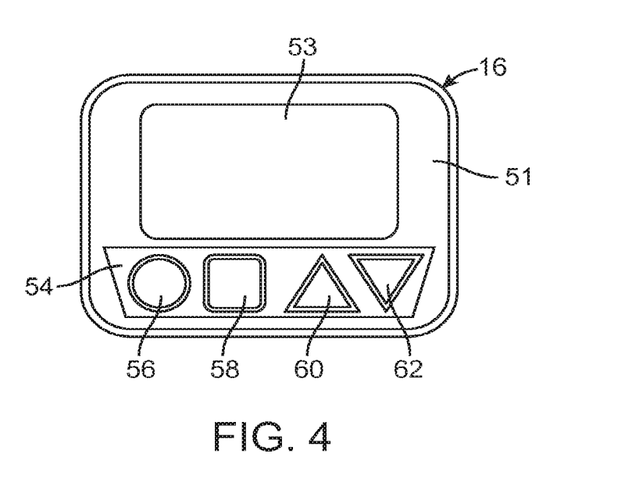
FIG. 4 is a plan view of a remote control that can be used in the SCS system of FIG. 1.

Referring now to FIG. 4, one exemplary embodiment of an RC 16 will now be described. As previously discussed, the RC 16 is capable of communicating with the IPG 14, CP 18, or ETS 20. The RC 16 comprises a casing 51, which houses internal componentry (including a printed circuit board (PCB)), and a lighted display screen 53 and button pad 54 carried by the exterior of the casing 51. In the illustrated embodiment, the display screen 53 is a lighted flat panel display screen, and the button pad 54 comprises a membrane switch with metal domes positioned over a flex circuit, and a keypad connector connected directly to a PCB. In an optional embodiment, the display screen 53 has touchscreen capabilities. The button pad 54 includes a multitude of buttons 56, 58, 60, and 62, which allow the IPG 14 to be turned ON and OFF, provide for the adjustment or setting of stimulation parameters within the IPG 14, and provide for selection between screens. Further details of the functionality and internal componentry of the RC 16 are disclosed in U.S. Pat. No. 6,895,280, which has previously been incorporated herein by reference.

Figure 5:
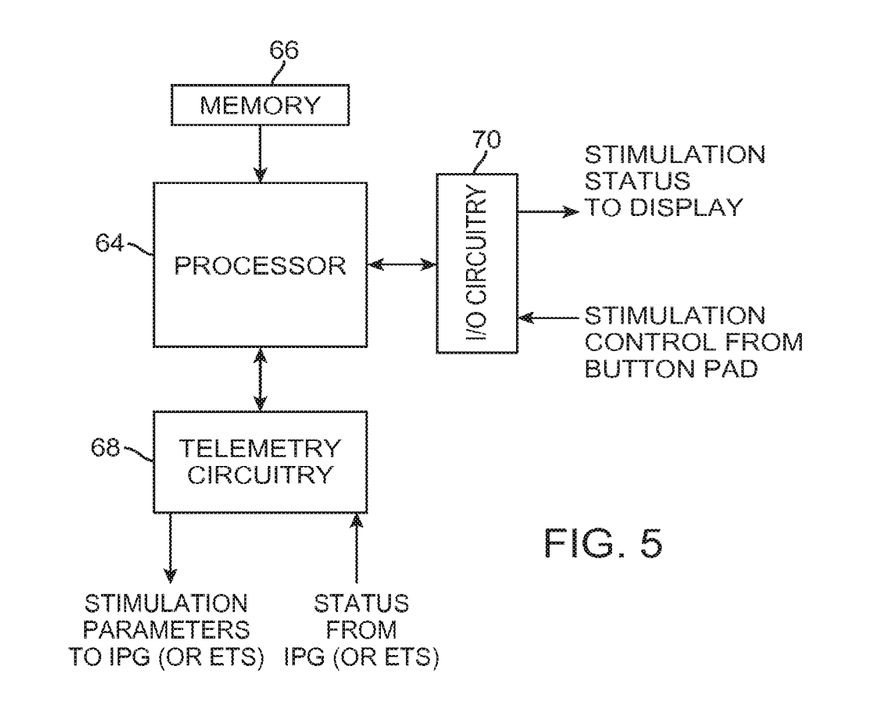
FIG. 5 is a block diagram of the internal componentry of the remote control of FIG. 4.

Referring to FIG. 5, the internal components of an exemplary RC 16 will now be described. The RC 16 generally includes a processor 64 (e.g., a microcontroller), memory 66 that stores an operating program for execution by the processor 64, as well as stimulation parameter sets, input/output circuitry, and in particular, telemetry circuitry 68 for outputting stimulation parameters to the IPG 14 and receiving status information from the IPG 14, and input/output circuitry 70 for receiving stimulation control signals from the button pad 54 and transmitting status information to the display screen 52 (shown in FIG. 4). As well as controlling other functions of the RC 16, which will not be described herein for purposes of brevity, the processor 64 generates new stimulation parameter sets in response to the user operation of the button pad 54. These new stimulation parameter sets would then be transmitted to the IPG 14 via the telemetry circuitry 68. Further details of the functionality and internal componentry of the RC 16 are disclosed in U.S. Pat. No. 6,895,280, which has previously been incorporated herein by reference.

As briefly discussed above, the CP 18 greatly simplifies the programming of multiple electrode combinations, allowing the user (e.g., the physician or clinician) to readily determine the desired stimulation parameters to be programmed into the IPG 14, as well as the RC 16. Thus, modification of the stimulation parameters in the programmable memory of the IPG 14 after implantation is performed by a user using the CP 18, which can directly communicate with the IPG 14 or indirectly communicate with the IPG 14 via the RC 16. That is, the CP 18 can be used by the user to modify operating parameters of the electrode array 26 near the spinal cord.

As shown in FIG. 2, the overall appearance of the CP 18 is that of a laptop personal computer (PC), and in fact, may be implemented using a PC that has been appropriately configured to include a directional-programming device and programmed to perform the functions described herein. Alternatively, the CP 18 may take the form of a mini-computer, personal digital assistant (PDA), etc., or even a remote control (RC) with expanded functionality. Thus, the programming methodologies can be performed by executing software instructions contained within the CP 18. Alternatively, such programming methodologies can be performed using firmware or hardware. In any event, the CP 18 may actively control the characteristics of the electrical stimulation generated by the IPG 14 to allow the optimum stimulation parameters to be determined based on patient feedback and for subsequently programming the IPG 14 with the optimum stimulation parameters.

To allow the user to perform these functions, the CP 18 includes a user interface. In the illustrated embodiment, the user interface of the CP 18 includes a mouse 72, a keyboard 74, and a programming display screen 76 housed in a case 78. It is to be understood that in addition to, or in lieu of, the mouse 72, other directional programming devices may be used, such as a trackball, touchpad, joystick, or directional keys included as part of the keys associated with the keyboard 74.

In the illustrated embodiment described below, the display screen 76 takes the form of a conventional screen, in which case, a virtual pointing device, such as a cursor controlled by a mouse, joy stick, trackball, etc, can be used to manipulate graphical objects on the display screen 76. In alternative embodiments, the display screen 76 takes the form of a digitizer touch screen, which may be either passive or active. If passive, the display screen 76 includes detection circuitry that recognizes pressure or a change in an electrical current when a passive device, such as a finger or non-electronic stylus, contacts the screen. If active, the display screen 76 includes detection circuitry that recognizes a signal transmitted by an electronic pen or stylus. In either case, detection circuitry is capable of detecting when a physical pointing device (e.g., a finger, a non-electronic stylus, or an electronic stylus) is in close proximity to the screen, whether it be making physical contact between the pointing device and the screen or bringing the pointing device in proximity to the screen within a predetermined distance, as well as detecting the location of the screen in which the physical pointing device is in close proximity. When the pointing device touches or otherwise is in close proximity to the screen, the graphical object on the screen adjacent to the touch point is "locked" for manipulation, and when the pointing device is moved away from the screen the previously locked object is unlocked.

Figure 6:
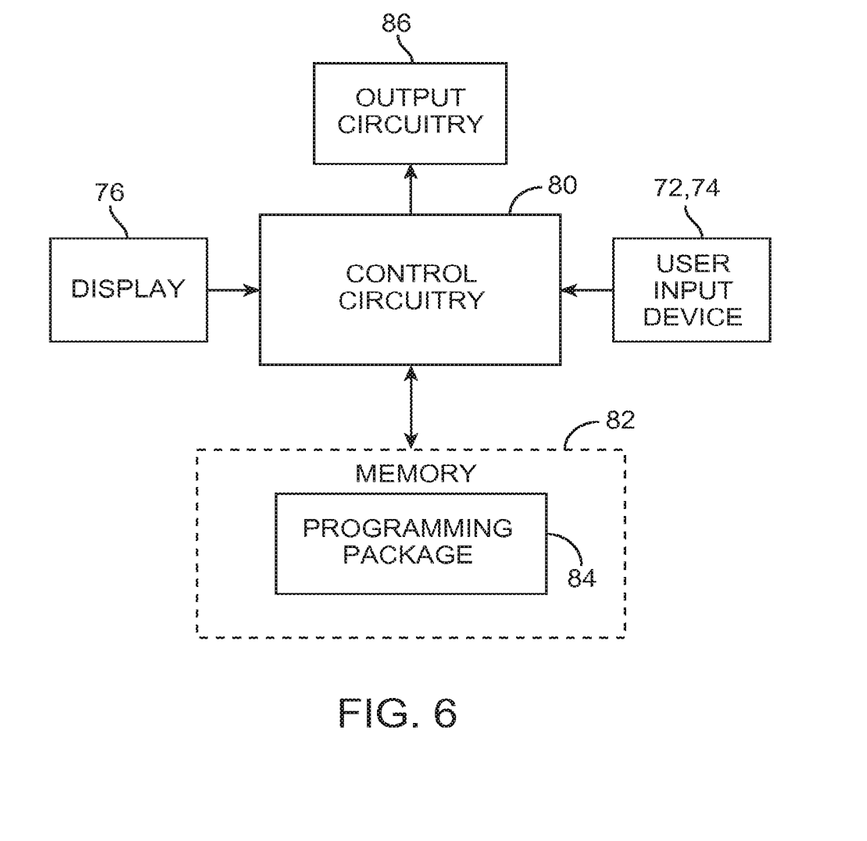
FIG. 6 is a block diagram of the components of a clinician programmer that can be used in the SCS system of FIG. 1.

As shown in FIG. 6, the CP 18 generally includes control circuitry 80 (e.g., a central processor unit (CPU)) and memory 82 that stores a stimulation programming package 84, which can be executed by the control circuitry 80 to allow the user to program the IPG 14, and RC 16. The CP 18 further includes output circuitry 86 for downloading (e.g., via the telemetry circuitry of the RC 16) stimulation parameters to the IPG 14 and RC 16 and for uploading stimulation parameters already stored in the memory 66 of the RC 16, via the telemetry circuitry 68 of the RC 16.

Execution of the programming package 84 by the control circuitry 80 provides a multitude of display screens (not shown) that can be navigated through via use of the pointing device. These display screens allow the clinician to, among other functions, select or enter patient profile information (e.g., name, birth date, patient identification, physician, diagnosis, and address), enter procedure information (e.g., programming/follow-up, implant trial system, implant IPG, implant IPG and lead(s), replace IPG, replace IPG and leads, replace or revise leads, explant, etc.), generate a pain map of the patient, define the configuration and orientation of the leads, initiate and control the electrical stimulation energy output by the neurostimulation leads 12, and select and program the IPG 14 with stimulation parameters in both a surgical setting and a clinical setting. Further details discussing the above-described CP functions are disclosed in U.S. Patent Application Publication No. 2010/0010566, entitled "System and Method for Converting Tissue Stimulation Programs in a Format Usable by an Electrical Current Steering Navigator," and U.S. Patent Application Publication No. 2010/0121409, entitled "System and Method for Determining Appropriate Steering Tables for Distributing Stimulation Energy Among Multiple Neurostimulation Electrodes," which are expressly incorporated herein by reference.

Most pertinent to the present inventions, execution of the programming package 84 provides a user interface that conveniently displays stimulation parameter sets along with indicators that indicate whether each stimulation parameter set is available to the patient from the RC 16. Thus, a user can quickly, easily, and conveniently determine right from the user interface whether a stimulation parameter set is available to the patient via the RC 16. Further, from the user interface, the user can quickly, easily, and conveniently instruct the control circuitry 80 to make a previously unavailable stimulation parameter set available to the patient via the RC 16, and/or to make a previously available stimulation parameter set unavailable to the patient.

Figure 7:
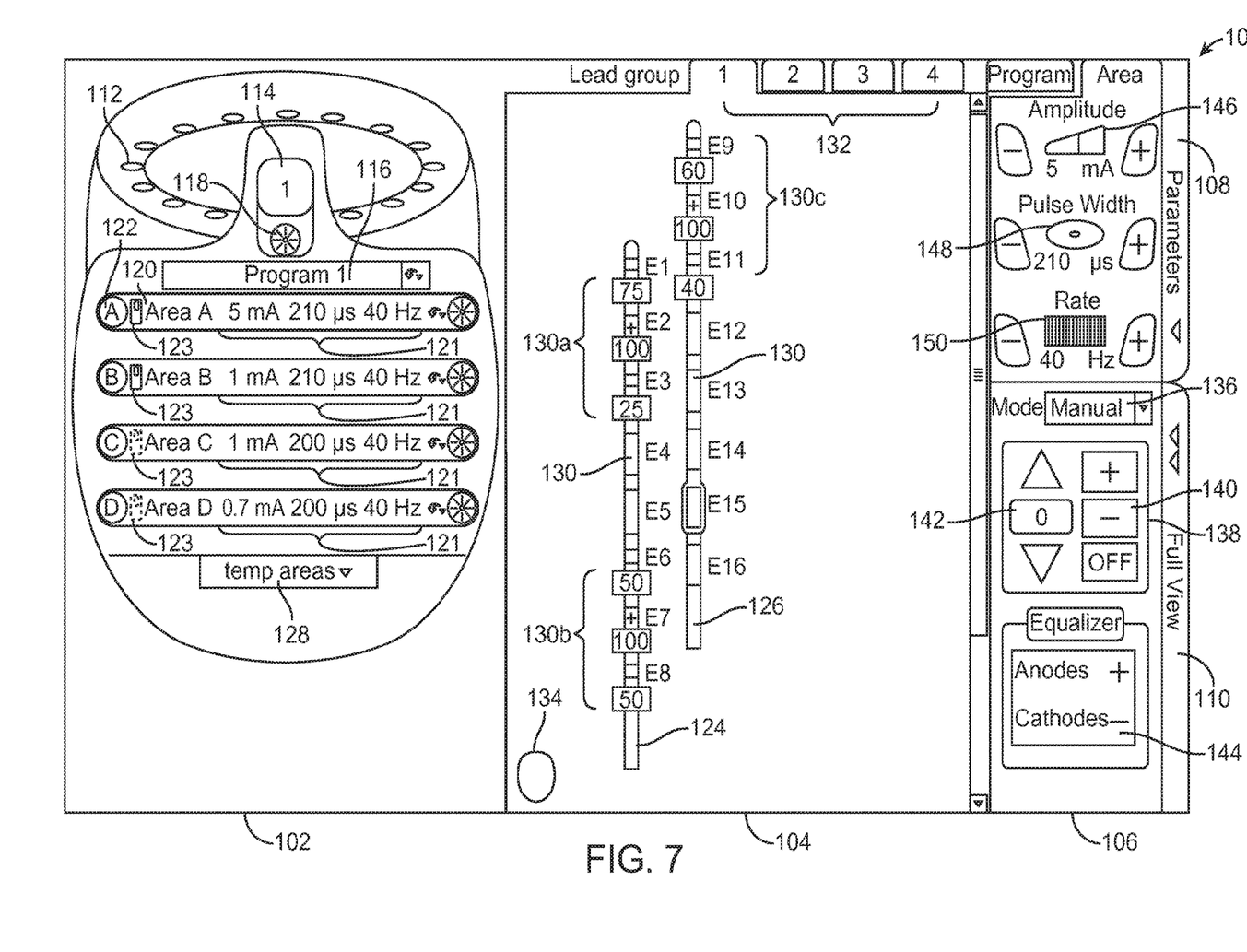
FIG. 7 is a plan view of a user interface of the CP of FIG. 6 for programming the IPG of FIG. 3 in a manual mode.

Referring now to FIG. 7, a graphical user interface (GUI) 100 that can be generated by the CP 18 to allow a user to program the IPG 14 will be described. In the illustrated embodiment, the GUI 100 comprises three panels, a program selection panel 102, a lead display panel 104, and an electrical parameter adjustment panel 106. Some embodiments of the GUI 100 may allow for closing and expanding one or both of the lead display panel 104 and the parameter adjustment panel 106 by clicking on the tab 108 (to show or hide the parameter adjustment panel 106) or the tab 110 (to show or hide the full view of both the lead display panel 104 and the parameter adjustment panel 106).

The program selection panel 102 provides information about programs and areas that have been, or may be, defined for the IPG 14. A plurality of programs may be displayed in carousel 112. In the illustrated embodiment, sixteen programs may be defined, but program 1 is the only one currently defined, as shown by the "1" in field 114. Other embodiments may use a carousel or other techniques for displaying available programs with different numbers or arrangements of available program slots.

Each program may be named, as indicated by the name field 116. A stimulation on/off button 118 allows turning the currently active program on or off. When the active program is on, stimulation parameter sets will be generated in the CP 18 and transmitted to the RC 16. Up to four program areas 120 may be defined, allowing a program to control stimulation of multiple areas. Each program area 120 may separately control stimulation of electrodes in the patient, and may be separately turned on or off. Each of the program areas 120 may be labeled with a label 122 that may be used as a marker on the graphical leads 124 and 126, as described below. A number of temporary areas 128 may be used for temporary storage of area information by copying a program area 120 into a temporary area 128 or copying a temporary area 128 into a program area 120. This allows copying a program area 120 from one of the four slots to another slot via one of the temporary areas 128. Other embodiments may also allow copying one of the program areas 120 into another one of the program areas 120 directly. Individual programs may be copied to other slots in the carousel 112 or deleted as desired.

Each of the program areas 120 includes a stimulation parameter set 121. An indicator 123 is displayed along with each stimulation parameter set 121, such that each displayed stimulation parameter set 121 is associated with an indicator 123 that can selectively be turned on or off by the user. In the embodiment shown in FIG. 7, each indicator 123 is an icon, which is a graphical depiction of a remote control. However, it should be well understood that the indicator may alternatively be any shape or format that may be selectively actuated by the user in order to turn the indicator on or off. For example, the indicator may be a radio button, check box, or the like.

The indicator 123 being on, actuated, or highlighted, as shown in "Area A" and "Area B" of the exemplary GUI 100, indicates that the stimulation parameter set 121 associated with the indicator 123 is currently available, or is to be made available, to the patient via the RC 16. The indicator 123 being off, un-actuated, un-highlighted, or grayed out, as shown in "Area C" and "Area D" of the exemplary GUI 100, indicates that the stimulation parameter set 121 associated with the indicator 123 is currently unavailable, or is to be made unavailable, to the patient via the RC 16. When a stimulation parameter set 121 is not available to the patient via the RC 16, that stimulation parameter set 121 may still be programmed into the IPG 14, but "locked" at the RC 16 to make it unavailable to the patient. For example, the program including all four stimulation parameter sets 121 may be programmed into the RC 16. However, only those stimulation parameter sets 121 associated with an indicator 123 that has been turned on (e.g., Area A and Area B shown in FIG. 7) will be made available to the patient via the RC 16. Those stimulation parameter sets 121 associated with an indicator 123 that has been turned off (e.g., Area C and Area D shown in FIG. 7) will be made unavailable to the patient from the RC 16 by "locking" them. Alternatively, a stimulation parameter set 121 may be made unavailable to the patient from the RC 16 by not programming the stimulation parameter set 121 into the IPG 14 at all.

From the GUI 100, a clinician may actuate the indicator 123 using a pointing device (e.g., a cursor, finger, stylus, etc.), thereby selectively turning the indicator 123 on or off. By actuating an indicator 123 that is already on, the user turns the indicator 123 off, thereby instructing the control circuitry 80 to make a previously available stimulation parameter set 121 unavailable to the patient from the RC 16. By actuating an indicator 123 that is already off, the user turns the indicator 108 on, thereby instructing the control circuitry 80 to make a previously unavailable stimulation parameter set 121 available to the patient from the RC 16.

In response to additional input from the clinician, the control circuitry 80 is configured to program the IPG 14 with all of the stimulation parameter sets 121 displayed on the GUI 100. The control circuitry 80 is further configured for making available to the patient via the RC 16 only those stimulation parameter sets 121 programmed into the RC 16 that are associated with an indicator 123 that has been turned on. Alternatively, rather than programming the IPG 14 with stimulation parameter sets, the control circuitry 80 may be configured to program the RC 16 with only those stimulation parameter sets 121 associated with an indicator 123 that has been turned on.

Turning now to the lead display panel 104, graphical leads 124 and 126 are illustrated with eight graphical electrodes 130 each (labeled electrodes E1-E8 for lead 124 and electrodes E9-E16 for lead 126). Other numbers of leads and electrodes per lead may be displayed as desired. In an implanted system using other numbers of electrodes, that number of electrodes may be shown in lead display panel 104. Up to four groups of leads may be viewed by selecting one of the lead group tabs 132. In addition, an icon 134 representing the case 50 of the IPG 14 is displayed in the lead display panel 104. In addition to allocating current to any of the electrodes of graphical leads 124 and 126, current may be allocated to the case 50 as an electrode.

Each of the electrodes 130 of the leads 124 and 126 may be individually selected, allowing the clinician to set the polarity and the magnitude of the current allocated to that electrode 130. In the illustrated embodiment, electrode E15 is currently selected. Electrical current has been allocated to three groups of electrodes respectively corresponding to three programming areas. Electrode group 130a illustrates a single cathode at electrode E2 to which is allocated 100% of the cathodic current and two anodes at electrodes E1 and E3 to which are allocated 25% and 75% of the anodic current, respectively. Electrode group 130b illustrates a single anode at electrode E7 to which is allocated 100% of the cathodic current and two anodes at electrodes E6 and E8 to which are allocated 50% and 50% of the anodic current, respectively. Electrode group 130c illustrates a single cathode at electrode E10 to which is allocated 100% of the cathodic current and two anodes at electrodes E9 and E11 to which are allocated 60% and 40% of the anodic current, respectively.

The parameter adjustment panel 106 includes a pull-down programming mode field 136 that allows the user to switch between a manual programming mode, an e-troll programming mode, and a Navigation programming mode. As shown in FIG. 7, the manual programming mode has been selected. In the manual programming mode, each of the electrodes 130 of the graphical leads 124 and 126, as well as the graphical case 134, may be individually selected, allowing the clinician to set the polarity (cathode or anode) and the magnitude of the current (percentage) allocated to that electrode 130 using graphical controls located in the amplitude/polarity area 138. In particular, a graphical polarity control 140 located in the area 138 includes a "+" icon, a "−" icon, and an "OFF" icon, which can be respectively actuated to toggle the selected electrode 130 between a positive polarization (anode), a negative polarization (cathode), and an off-state. An amplitude control 142 in the area 138 includes an arrow that can be actuated to decrease the magnitude of the fractionalized current of the selected electrode 130, and an arrow that can be actuated to increase the magnitude of the fractionalized current of the selected electrode 130. The amplitude control 142 also includes a display area that indicates the adjusted magnitude of the fractionalized current for the selected electrode 130. Amplitude control 142 is preferably disabled if no electrode is visible and selected in the lead display panel 104.

The parameter adjustment panel 106, when the manual programming mode is selected, also includes an equalization control 144 that can be actuated to automatically equalize current allocation to all electrodes of a polarity selected by respective "Anode +" and "Cathode −" icons. The parameter adjustment panel 106 also includes a pulse amplitude adjustment control 146 (expressed in milliamperes (mA)), a pulse width adjustment control 148 (expressed in microseconds (μs)), and a pulse rate adjustment control 150 (expressed in Hertz (Hz)), which are displayed in all three of the programming modes. Each of the controls 146, 148, 150 includes a first arrow that can be actuated to decrease the value of the respective stimulation parameter and a second arrow that can be actuated to increase the value of the respective stimulation parameter. Each of the controls 146, 148, 150 also includes a display area for displaying the currently selected parameter. In the illustrated embodiment, a pulse amplitude of 5 mA, a pulse width of 210 μs, a pulse rate of 40 Hz have been selected.

Figure 8:
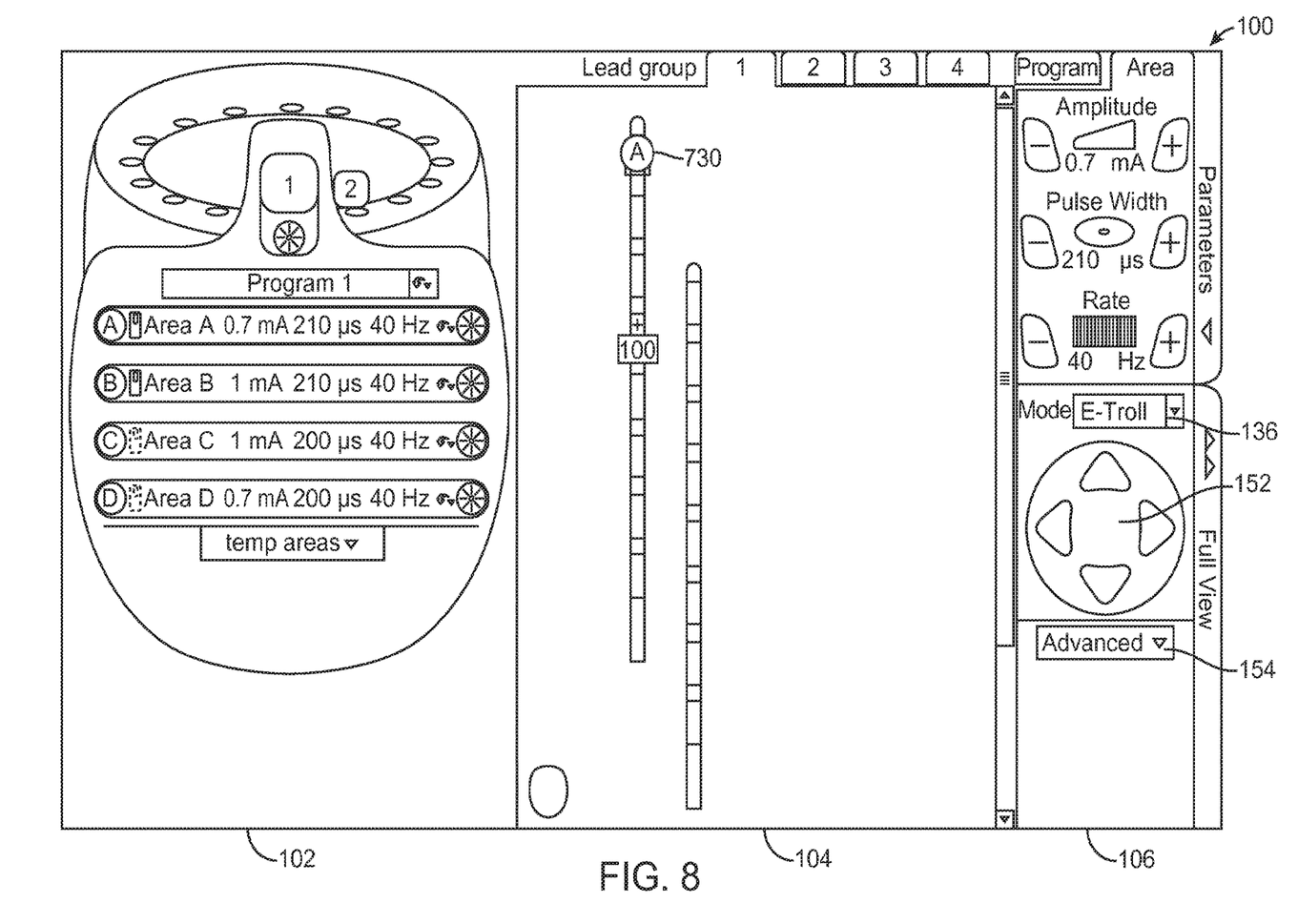
FIG. 8 is a plan view of a user interface of the CP of FIG. 6 for programming the IPG of FIG. 3 in an e-troll mode.

As shown in FIG. 8, the e-troll programming mode has been selected. In this mode, the electrodes 130 illustrated in the lead display panel 104 that were individually selectable and configurable in manual programming mode are used for display only and are not directly selectable or controllable. The parameter selection panel 106 includes a steering array of arrows 152 that allows steering the electrical current up, down, left, or right. In the illustrated embodiment, the electrical current is steered by panning a virtual multipole (i.e., the virtual multipole is moved relative to the actual electrodes 26 without changing the basic configuration (focus (F) and upper anode percentage (UAP)) of the virtual multipole), and computing the electrical amplitude values needed for the actual electrodes 26 to emulate the virtual multipole.

Figure 9:
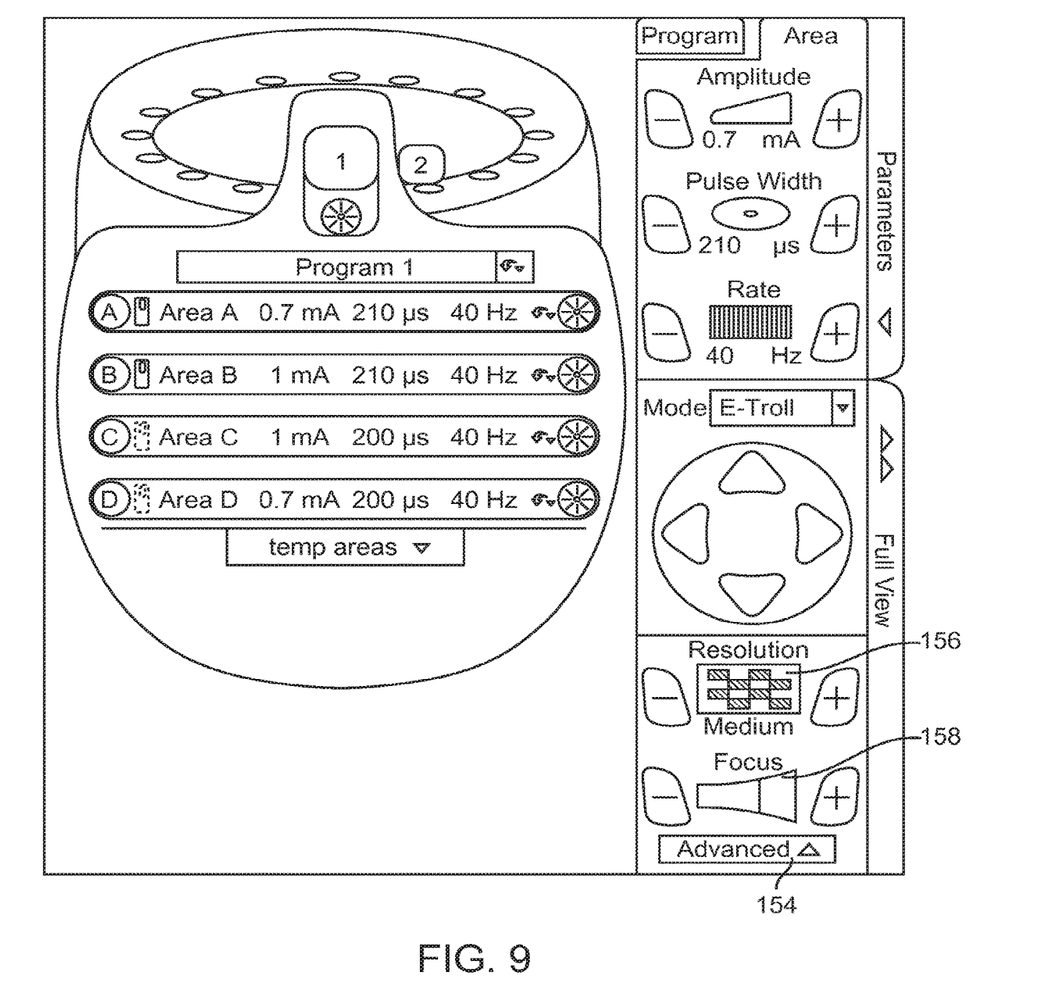
FIG. 9 is a plan view of the user interface of FIG. 8, particularly showing the expansion of the Advanced Tab into resolution and focus controls.

In the e-troll programming mode, the parameter adjustment panel 106 also includes an advanced tab 154, which when actuated, hides the lead display panel 104 and provides access to a resolution control 156 and a focus control 158, as shown in FIG. 9.

The resolution control 156 allows changing the stimulation adjustment resolution. In one embodiment, three possible settings of Fine, Medium, and Coarse may be chosen. The resolution control 156 has a "+" icon and a "−" icon that can be used to adjust the resolution. The resolution control 156 also includes a display element that graphically displays the current resolution level. When the resolution is set to Fine, each change caused by use of the steering array 152 makes less of a change to the electrode configuration than when the resolution is set to Medium or Coarse. For example, panning of the virtual multipole with a Coarse resolution may displace the virtual multipole relative to the electrode array 26 in steps equivalent to 10% of the electrode spacing, whereas panning of the virtual multipole with a Fine resolution may move the virtual multipole relative to the electrode array 26 in steps equivalent to 1% of the electrode spacing.

The focus control 158 allows changing the stimulation focus by displacing the anode(s) and cathode of the virtual multipole toward each other to increase the focus, or displacing the anode(s) and cathode of the virtual multipole away from each other to decrease the focus. The focus control 158 has a "+" icon and a "−" icon that can be used to adjust the focus. The resolution control 158 also includes a display element that graphically displays the current focus level.

Figure 10:
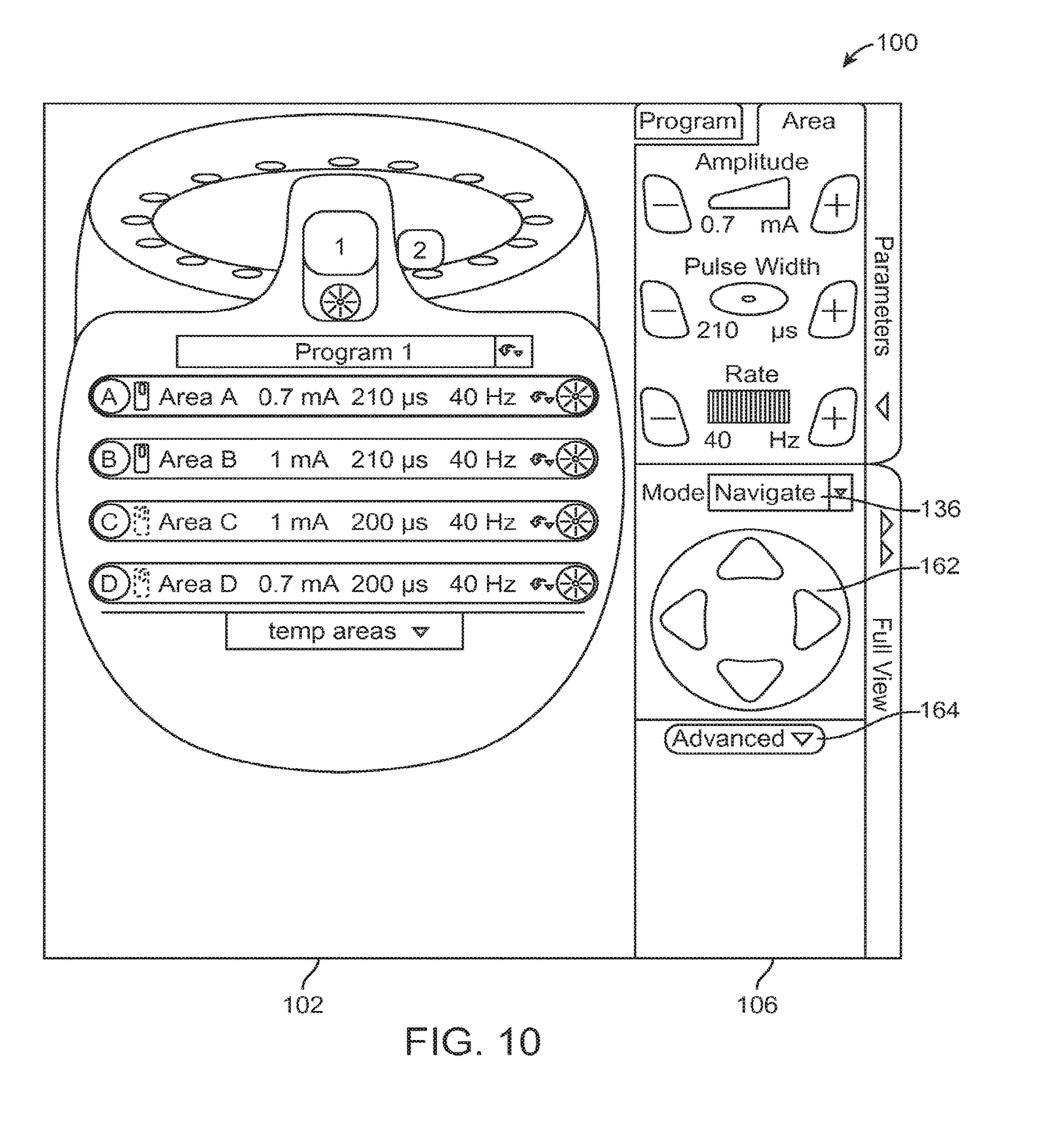
FIG. 10 is a plan view of a user interface of the CP of FIG. 6 for programming the IPG of FIG. 3 in a Navigation mode.

As shown in FIG. 10, the Navigation programming mode has been selected. As in the e-troll programming mode, in the Navigation programming mode, the electrodes illustrated in the lead display panel 104 that were individually selectable and configurable in manual programming mode are used for display only and are not directly selectable or controllable. The parameter selection panel 106 includes a steering array of arrows 162 that allows steering the electrical current up, down, left, or right. In the illustrated embodiment, the electrical current is steered by weaving one or more anodes around the cathode of the virtual multipole as the cathode is displaced relative to the electrode array 26, and computing the electrical amplitude values needed for the electrodes 26 to emulate the virtual multipole.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A method implemented using a system including a first external system, a second external system, and a neurostimulator programmed with at least one stimulation program, each of the at least one program having one or more stimulation parameter sets, each of the one or more stimulation parameter sets including parameter values for more than one neurostimulation parameter, the method comprising using the first external system to:
    program the second external system with a parameter set status for each of the one or more parameter sets, the parameter set status determining whether the second external system has access to modify corresponding ones of the one or more parameter sets;
    display the one or more stimulation parameter sets for a corresponding stimulation program;
    display one or more indicators corresponding to the one or more stimulation parameter sets, each of the one or more indicators indicating the parameter set status for a corresponding one of the displayed parameter sets for the corresponding stimulation program; and
    receive input from a user and, in response to the input from the user, selectively turn the indicator on or off for the corresponding one of the displayed parameter sets and program the second external system with the parameter set status for the corresponding one of the parameter sets according to whether the indicator is on or off.

2. The method of claim 1, wherein the neurostimulator is implantable in a patient, and the second external system is configured for use by the patient.

3. The method of claim 1, wherein the neurostimulator is implantable in a patient, and the first external system is configured for use by a medical provider.

4. The method of claim 1, wherein the first external system is a clinician programmer.

5. The method of claim 1, wherein the one or more of indicators include one or more icons.

6. The method of claim 1, wherein the receiving input from the user comprises actuating one of the one or more indicators.

7. A method performed using an external control device configured for use with a neurostimulator and a remote control, the method comprising using the external control device for:
   programming the neurostimulator with at least one stimulation program, each of the at least one program having one or more stimulation parameter sets, each of the one or more stimulation parameter sets including parameter values for more than one neurostimulation parameter;
   programming the remote control with a parameter set status for each of the one or more parameter sets, the parameter set status determining whether the remote control has access to modify corresponding ones of the one or more parameter sets;
   displaying the one or more stimulation parameter sets for a corresponding stimulation program;
   displaying one or more indicators corresponding to the one or more stimulation parameter sets, each of the one or more indicators indicating the parameter set status for a corresponding one of the displayed parameter sets for the corresponding stimulation program; and
   receiving input from a user and, in response to the input from the user, selectively turning the indicator on or off for the corresponding one of the displayed parameter sets and programming the remote control with the parameter set status for the corresponding one of the parameter sets according to whether the indicator is on or off.

8. The method of claim 7, wherein the one or more indicators include a one or more icons.

9. The method of claim 8, wherein the one or more icons include a graphical depiction of a remote control to indicate that the remote control has access to the parameter set to modify the stimulation program.

10. The method of claim 7, wherein the receiving input from the user comprises actuating one of the one or more indicators.

11. The method of claim 7, wherein the receiving input from the user includes using a digitizer screen for receiving the input from the user.

12. The method of claim 7, further comprising receiving other input from the user, and responding to the other input from the user by programming the neurostimulator with the stimulation parameter set.

13. The method of claim 7, further comprising receiving other input from the user, and responding to the other input from the user by programming the remote control with one of the one or more stimulation parameter sets.

14. The method of claim 7, further comprising selectively turning each of the indicators on or off in response to user input.

15. A non-transitory machine-readable medium including instructions, which when executed by a machine, cause the machine to implement a method performed using a system including a first external system, a second external system, and a neurostimulator programmed with at least one stimulation program, each of the at least one program having one or more stimulation parameter sets, each of the one or more stimulation parameter sets including parameter values for more than one neurostimulation parameter, the method comprising using the first external system to:
   program the second external system with a parameter set status for each of the one or more parameter sets, the parameter set status determining whether the second external system has access to modify corresponding ones of the one or more parameter sets;
   display one or more stimulation parameter sets for a corresponding stimulation program;
   display one or more indicators corresponding to the stimulation parameter sets, each of the one or more indicators indicating the parameter set status for a corresponding one of the displayed parameter sets for the corresponding stimulation program; and
   receive input from a user and, in response to the input from the user, selectively turn the indicator on or off for the corresponding one of the displayed parameter sets and program the second external system with the parameter set status for the corresponding one of the parameter sets according to whether the indicator is on or off.

16. The non-transitory machine-readable medium of claim 15, wherein the neurostimulator is implantable in a patient, and the second external system is configured for use by the patient.

17. The non-transitory machine-readable medium of claim 15, wherein the neurostimulator is implantable in a patient, and the first external system is configured for use by a medical provider.

18. The non-transitory machine-readable medium of claim 15, wherein the one or more indicators include one or more icons.

19. The non-transitory machine-readable medium of claim 18, wherein the one or more icons include a graphical depiction of the second external system to indicate that the second external system has access to the parameter set to modify the stimulation program.

20. The non-transitory machine-readable medium of claim 15, wherein the receive input from the user comprises actuate one of the indicators.

* * * * *